(12) United States Patent
Xiong et al.

(10) Patent No.: US 11,982,609 B1
(45) Date of Patent: May 14, 2024

(54) METHOD FOR DETERMINING LOWER RADIUS LIMIT OF MOVABLE THROAT OF SHALE

(71) Applicant: Southwest Petroleum University, Chengdu (CN)

(72) Inventors: Yu Xiong, Chengdu (CN); LingHong Wang, Kunming (CN); MeiHua Chen, Fushun (CN); TingTing Lei, Baoji (CN); MeiJuan Guo, Xianyang (CN); HaiTao Hong, Chengdu (CN); XiuQing Li, Chengdu (CN); Rui Zhang, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 18/476,338

(22) Filed: Sep. 28, 2023

(30) Foreign Application Priority Data

Nov. 4, 2022 (CN) .......................... 202211378693.9

(51) Int. Cl.
*G01N 15/08* (2006.01)
*G01N 1/44* (2006.01)
*G01N 24/08* (2006.01)
*G01N 33/24* (2006.01)

(52) U.S. Cl.
CPC ........... *G01N 15/0886* (2013.01); *G01N 1/44* (2013.01); *G01N 24/081* (2013.01); *G01N 33/24* (2013.01)

(58) Field of Classification Search
None
See application file for complete search history.

(56) References Cited

U.S. PATENT DOCUMENTS 7,825,659 B2 * 11/2010 Georgi ................ G01N 24/081
324/306

FOREIGN PATENT DOCUMENTS

| CN | 105974092 A | * | 9/2016 | ............ G01N 33/24 |
| CN | 111311575 A | * | 6/2020 | ........... G06T 7/0004 |
| CN | 113050188 A | * | 6/2021 | ............... G01V 9/00 |
| CN | 113740515 B | * | 3/2022 | ........... G01N 24/081 |
| CN | 114894692 A | | 8/2022 | |

* cited by examiner

*Primary Examiner* — Daniel S Larkin

(57) ABSTRACT

A method for determining lower radius limit of movable throat of shale is provided, and it includes: performing a low-temperature nitrogen adsorption test on a target shale to obtain first pore radii; performing a high-pressure mercury injection test on the target shale to obtain second pore radii; performing a nuclear magnetic resonance test on the target shale to obtain third pore radii; obtaining a relationship diagram of distribution frequencies and pore radii according to three pore radii; distinguishing, according to the pore radii, relationship diagram data, and performing normalization processing to determining a relationship curve of normalized frequency data and the pore radii; and determining a lower radius limit of movable throat of shale according to relationship curve. A problem of describing characteristics of shale occurrence space with complex pore structures and strong heterogeneity is solved, the method is suitable for determining lower radius limit of movable throat of shale.

5 Claims, 3 Drawing Sheets

METHOD FOR DETERMINING LOWER RADIUS LIMIT OF MOVABLE THROAT OF SHALE

TECHNICAL FIELD

The disclosure relates to the field of unconventional oil and gas reservoir development technologies, and more particularly to a method for determining a lower radius limit of a movable throat of shale.

BACKGROUND

The Jurassic Daanzhai shale reservoir in the Sichuan Basin mainly develops inorganic pores and microcracks, a reservoir and penetration space as a whole is characterized by coupling coexistence of pores and cracks with multi-causal and multi-scale, complex structures of the pores and cracks and a low quality characteristic of crude oil are jointly determine that structures of pores and cracks of shale reservoir (i.e., shale) has characteristics of diverse types and significant differences, thus a lower radius limit of a movable throat of the shale cannot be accurately characterized using one of a low-temperature nitrogen adsorption method and a single high-pressure mercury injection method.

At present, the low-temperature nitrogen adsorption method combined with the high-pressure mercury injection method is a commonly used method for characterizing a range of a full pore radius, and studies for characterizing a pore radius of the shale reservoir by combining the low-temperature nitrogen adsorption method and the high-pressure mercury injection method have attracted much attention. The low-temperature nitrogen adsorption method has advantages in analyzing micropores and mesopores of mud shale, and it can respectively perform detailed description on the micropores and the mesopores of the mud shale. The high-pressure mercury injection method is relatively less affected by uneven distribution of the pore radii of the mud shale, and thus the high-pressure mercury injection method can make up for a disadvantage of the low-temperature nitrogen adsorption method in analyzing of macrospores. A text range of a nuclear magnetic resonance (NMR) method is most extensive, and can be applied from the micropores to the microcracks, however, the nuclear magnetic resonance method is deficient in the characterization of the micropores and the mesopores. For boundaries of several test results, some researchers connect curves of two tests respectively corresponding to the low-temperature nitrogen adsorption method and the high-pressure mercury injection method with 100 nanometers (nm) as a boundary (in order to preserve a test result of the low-temperature nitrogen adsorption method), some researchers also consider an advantage of the high-pressure mercury injection method in a macropore characterization aspect and remain all results of the low-temperature nitrogen adsorption method, and 50 nm is selected as a boundary to connect the curves, however, a test result of the nuclear magnetic resonance method is not considered. In order to determine a more reasonable connecting boundary, the lower radius limit of the movable throat of the shale is obtained, the disclosure first proposes a combination of the low-temperature nitrogen adsorption—the high-pressure mercury injection—the nuclear magnetic resonance, and combines a movable oil extraction method to take a throat radius in a situation that a cumulative distribution frequency (from macropores to micropores) is equal to a movable oil saturation as the lower radius limit of the movable throat of the shale. Therefore, it is crucial to study a novel method for determining the lower radius limit of the movable throat of the shale.

SUMMARY

Aiming at the above disadvantages of the related art, the disclosure provides a method for determining a lower radius limit of a movable throat of shale, and problems of a disadvantage of a nitrogen adsorption method in macropores analysis and a disadvantage of a nuclear magnetic resonance method in characterization of micropores and mesopores are solved.

In order to achieve the above purpose of the disclosure, it provides a method for determining a lower radius limit of a movable throat of shale, and the method includes:

S1, performing a low-temperature nitrogen adsorption test on a target shale to obtain first pore radii of the target shale;

S2, performing a high-pressure mercury injection test on the target shale to obtain second pore radii of the target shale;

S3, performing a nuclear magnetic resonance test on the target shale to obtain third pore radii of the target shale;

S4, obtaining a relationship diagram of distribution frequencies and pore radii according to the first pore radii, the second pore radii and the third pore radii;

S5, distinguishing, according to the pore radii, data of the relationship diagram of the distribution frequencies and the pore radii to determine target frequency data, performing normalization processing on the target frequency data to obtain normalized frequency data, and determining a relationship curve of the normalized frequency data and the pore radii; and S6, determining a lower radius limit of the movable throat of shale according to the relationship curve of the normalized frequency data and the pore radii.

In an embodiment, step S1 specifically includes:

obtaining each of the first pore radii r according to a formula expressed as follows:

$$\ln \frac{p}{p_0} = \frac{2\gamma \bar{V}}{rRT} \cos \theta;$$

where $\bar{V}$ represents a molar volume of liquid; p represents a balance pressure; $p_0$ represents a saturation balance pressure; γ represents a surface tension of liquid nitrogen; R represents a universal gas constant; T represents an absolute temperature; and θ represents an angle between an adsorbate and an adsorbent.

In an embodiment, step S2 specifically includes:

simulating, by using a standard non-wet-phase fluid mercury, crude oil to perform the high-pressure mercury injection test on to thereby obtain each of the second pore radii r' according to a formula expressed as follows:

r'=2σ cos θ'/Pc;

where Pc represents a capillary pressure; θ' represents a wetting angle between mercury and the target shale; and α represents an interface tension between the mercury and air.

In an embodiment, step S3 specifically includes:

performing the nuclear magnetic resonance test on a standard plunger sample of the target shale vacuumed for 24 hours and saturated with 12 megapascals (MPa) pressure for 72 hours to thereby obtain each of the third pore radii r" according to a formula expressed as follows:

$$r'' = T_2 \rho_2 F_s;$$

where $T_2$ represents a T2 relaxation time of nuclear magnetic resonance; $F_s$ represents a dimensionless shape factor, wherein $F_s=2$; and $\rho_2$ represents a surface relaxation rate.

In an embodiment, step S5 specifically includes:

S5-1, for the pore radii being in a range of 0-100 nanometers (nm), taking an intersection of a low-temperature nitrogen adsorption curve and a high-pressure mercury injection curve as a first demarcation point of the low-temperature nitrogen adsorption curve and the high-pressure mercury injection curve, determining the low-temperature nitrogen adsorption curve as a curve before the first demarcation point, and determining the high-pressure mercury injection curve as a curve after the first demarcation point; and for the pore radii being in a range of 100-2000 nm, taking an intersection of the high-pressure mercury injection curve and a nuclear magnetic resonance curve as a second demarcation point of the high-pressure mercury injection curve and the nuclear magnetic resonance curve, determining the high-pressure mercury injection frequency as a curve before the second demarcation point, and determining the nuclear magnetic resonance curve as a curve after the second demarcation point; and thereby obtaining three-segment pore radius-distribution frequency data;

S5-2, summing the three-segment pore radius-distribution frequency data to obtain a sum, taking the sum as a denominator, taking a distribution frequency of each of the pore radii as a numerator, and dividing the denominator by the numerator and multiplying by 100 percent (%) to obtain the normalized frequency data; and S5-3, obtaining the relationship curve of the normalized frequency data and the pore radii according to the normalized frequency data.

In an embodiment, step S6 specifically includes:

S6-1, saturating a core of the target shale with crude oil to obtain a saturated core;

S6-2, heating and extracting the saturated core by using petroleum ether as an oil washing solvent to obtain shale oil, and taking a percentage of a volume of the shale oil volume to a pore volume of the core as a movable oil saturation; and S6-3, summing distribution frequencies corresponding to pore radii from large to small in sequence according to the relationship curve of the normalized frequency data and the pore radii to obtain a cumulative distribution frequency from large to small pores; in a situation that the cumulative distribution frequency from large to small pores is equal to the movable oil saturation, obtaining a corresponding throat radius as the lower radius limit of movable throat of the target shale.

Beneficial effects of the disclosure are as follows.

The disclosure considers pore structure characteristics of actual shale, and the pore structure characteristics from micropores to microcracks are involved. The disclosure can solve a problem of describing a characteristic of shale occurrence space with a complex pore structure and a strong heterogeneity, and the disclosure lays a foundation for precise evaluation of shale oil mobility. The method of the disclosure is easy to implement, has higher accuracy, and the method is more suitable for determining a lower radius limit of a movable throat of an unconventional oil reservoir, especially shale.

DETAILED DESCRIPTION OF EMBODIMENTS

An embodiment of the disclosure will be described below to be convenient for those skilled in the art to understand the disclosure. However, it should be clear that the disclosure is not limited in a range of the embodiment. For those skilled in the art, as long as various changes are within a spirit and a scope of the disclosure as defined and determined by attached claims, these changes are obvious, and all inventions and creations that utilize a concept of the disclosure are under protection.

Figure 1:
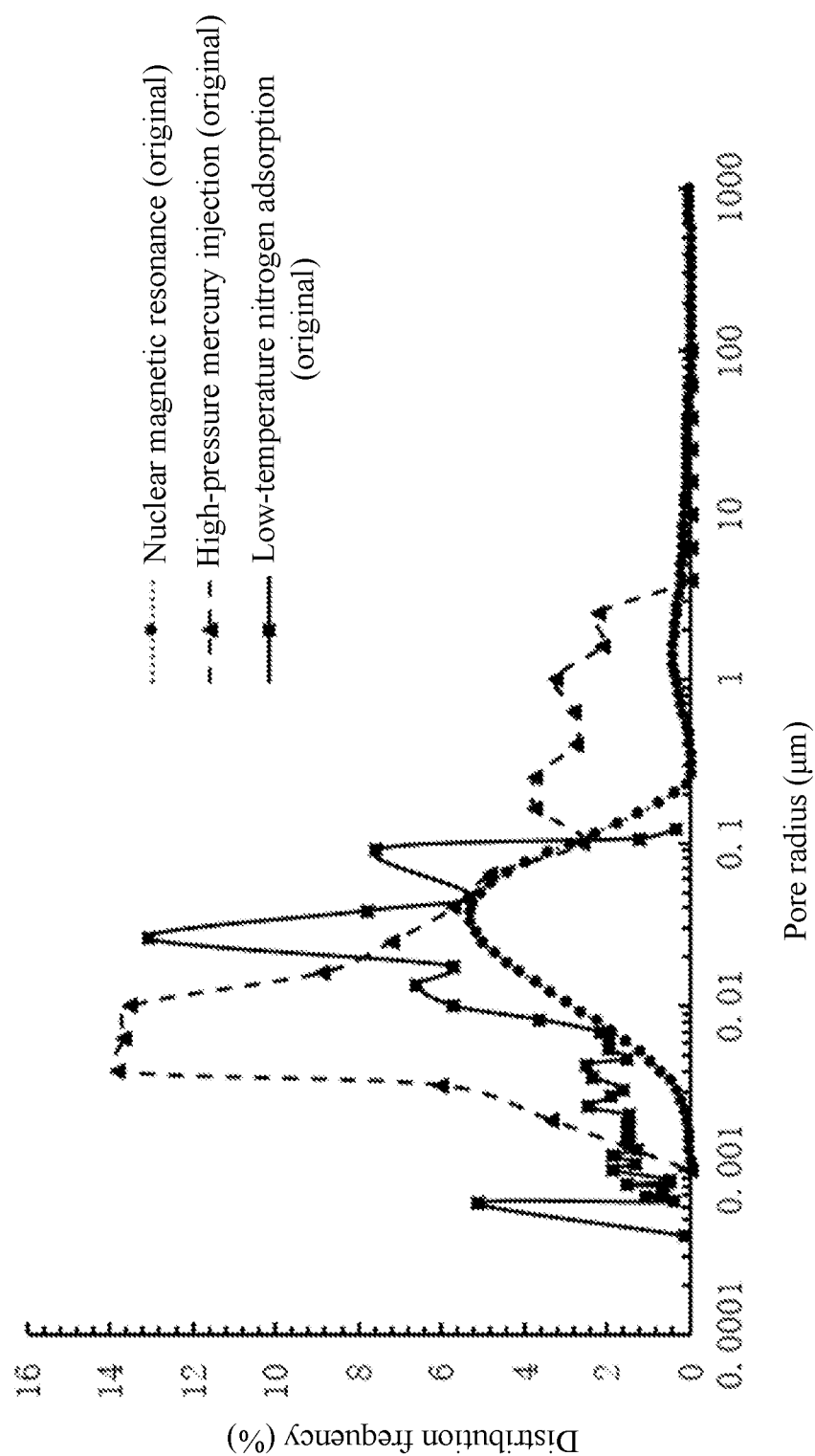
FIG. 1 illustrates a schematic diagram showing a relationship between distribution frequencies and pore radii according to an embodiment of the disclosure.

As shown in FIG. 1, a method for determining a lower radius limit of a movable throat of shale is provided, and the method includes the following steps S1-S6.

In step S1, a low-temperature nitrogen adsorption test is performed on a target shale to obtain first pore radii of the target shale.

In step S2, a high-pressure mercury injection test is performed on the target shale to obtain second pore radii of the target shale.

In step S3, a nuclear magnetic resonance test is performed on the target shale to obtain third pore radii of the target shale.

In step S4, a relationship diagram of distribution frequencies and pore radii of the target shale is obtained according to the first pore radii, the second pore radii and the third pore radii.

In step S5, data of the relationship diagram of the distribution frequencies and the pore radii is distinguished according to the pore radii to determine target frequency data, normalization processing is performed on the target frequency data to obtain normalized frequency data, and a relationship curve of the normalized frequency data and the pore radii is determined.

In step S6, a lower radius limit of a movable throat of the target shale is determined according to the relationship curve of the normalized frequency data and the pore radii.

In an embodiment, step S1 specifically includes the following steps.

Each of the first pore radii r is obtained according to a formula expressed as follows:

$$\ln \frac{p}{p_0} = \frac{2\gamma \bar{V}}{rRT} \cos \theta;$$

where $\overline{V}$ represents a molar volume of liquid; p represents a balance pressure; $p_0$ represents a saturation balance pressure; γ represents a surface tension of liquid nitrogen; R represents a universal gas constant; T represents an absolute temperature; and θ represents an angle between an adsorbate and an adsorbent.

In an embodiment, step S2 specifically includes the following steps.

Crude oil is simulated by using a standard non-wet-phase fluid mercury, to perform the high-pressure mercury injection test to thereby obtain each of the second pore radii r' according to a formula expressed as follows:

$$r'=2\sigma \cos \theta'/Pc;$$

where Pc represents a capillary pressure; θ' represents a wetting angle between mercury and the target shale; and α represents an interface tension between the mercury and air.

In an embodiment, step S3 specifically includes the following steps.

A standard plunger sample of the target shale is vacuumed for 24 hours and saturated with 12 megapascals (MPa) pressure for 72 hours, and the nuclear magnetic resonance test is performed on the standard plunger sample to thereby obtain each of the third pore radii r" according to a formula expressed as follows:

$$r''=T_2\rho_2F_s;$$

where $T_2$ represents a T2 relaxation time (i.e., transverse relaxation time) of nuclear magnetic resonance; $F_s$ represents a dimensionless shape factor, wherein $F_s=2$; and $\rho_2$ represents a surface relaxation rate.

Figure 2:
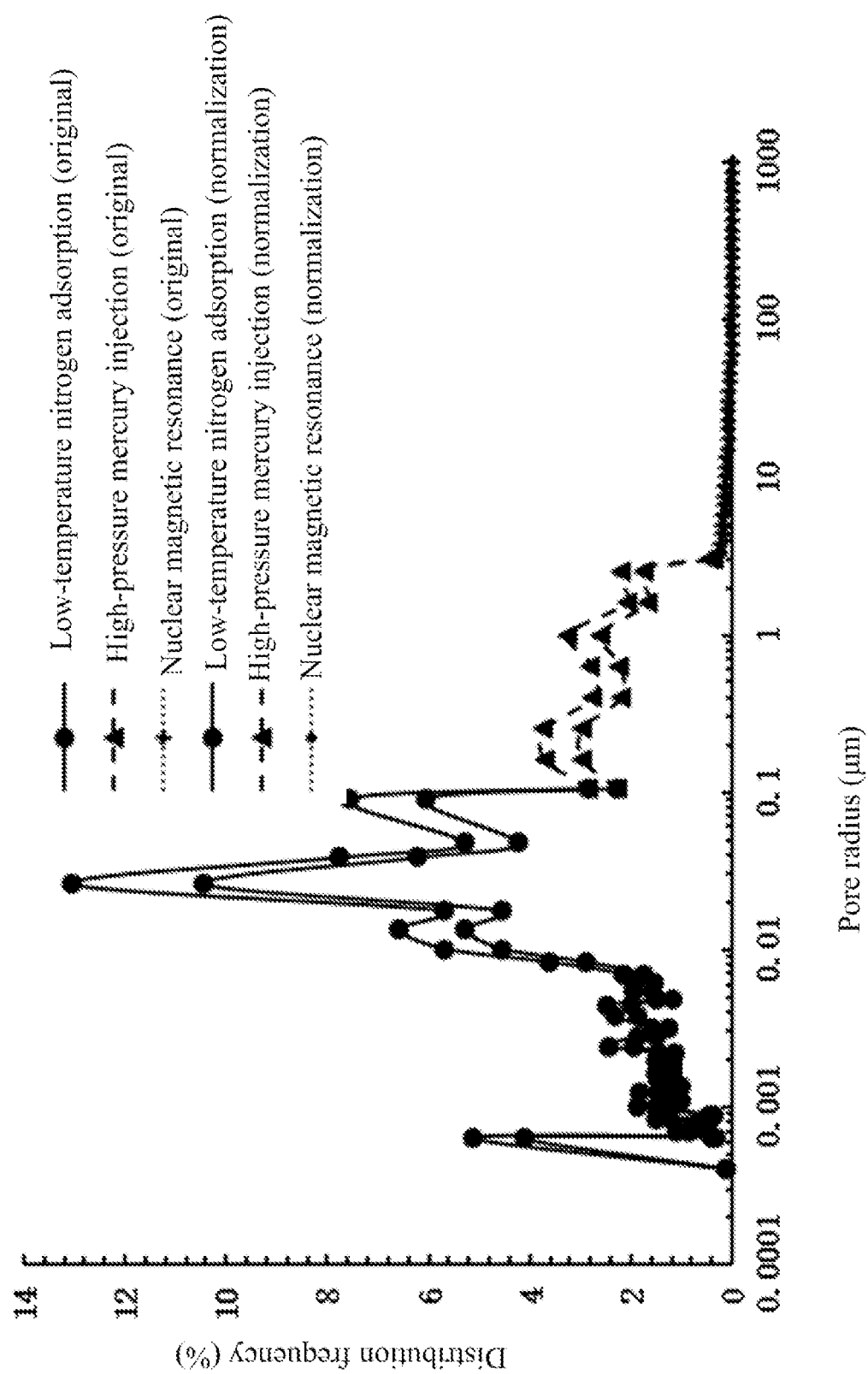
FIG. 2 illustrates a schematic diagram showing a connected relationship curve of normalized frequency data and pore radii of shale of different test methods according to an embodiment of the disclosure.

As shown in FIG. 2, step S5 specifically includes the following steps S5-1 to S5-3.

In step S5-1, for the pore radii being in a range of 0-100 nanometers (nm), an intersection of a low-temperature nitrogen adsorption curve and a high-pressure mercury injection curve is taken as a first demarcation point of the low-temperature nitrogen adsorption curve and the high-pressure mercury injection curve, the low-temperature nitrogen adsorption curve is determined as a curve before the first demarcation point, and the high-pressure mercury injection curve is determined as a curve after the first demarcation point.

Furthermore, in step S5-1, for the pore radii being in a range of 100-2000 nm, an intersection of the high-pressure mercury injection curve and a nuclear magnetic resonance curve is taken as a second demarcation point of the high-pressure mercury injection curve and the nuclear magnetic resonance curve, the high-pressure mercury injection curve is determined as a curve before the second demarcation point, and the nuclear magnetic resonance curve is determined as a curve after the second demarcation point; and three-segment pore radius-distribution frequency data is thereby obtained.

In step S5-2, the three-segment pore radius-distribution frequency data is summed to obtain a sum, and the sum is taken as a denominator, a distribution frequency of each of the pore radii is taken as a numerator, the denominator is divided by the numerator and is multiplied by 100 percent (%) to thus obtain the normalized frequency data.

In step S5-3, the relationship curve of the normalized frequency data and the pore radii is obtained according to the normalized frequency data.

In an embodiment, step S6 specifically includes the following steps S6-1-S6-3.

In step S6-1, a core of the target shale is saturated with crude oil to obtain a saturated core.

In step S6-2, the saturated core is heated and extracted by using petroleum ether as an oil washing solvent to obtain shale oil; and a percentage of a volume of the shale oil to a pore volume of the core is taken as a movable oil saturation.

In step S6-3, distribution frequencies corresponding to pore radii from large to small are summed in sequence according to the relationship curve of the normalized frequency data and the pore radii to obtain a cumulative distribution frequency from large to small pores; in a situation that the cumulative distribution frequency from large to small pores is equal to the movable oil saturation, a corresponding throat radius is obtained as the lower radius limit of the movable throat of the target shale.

Figure 3:
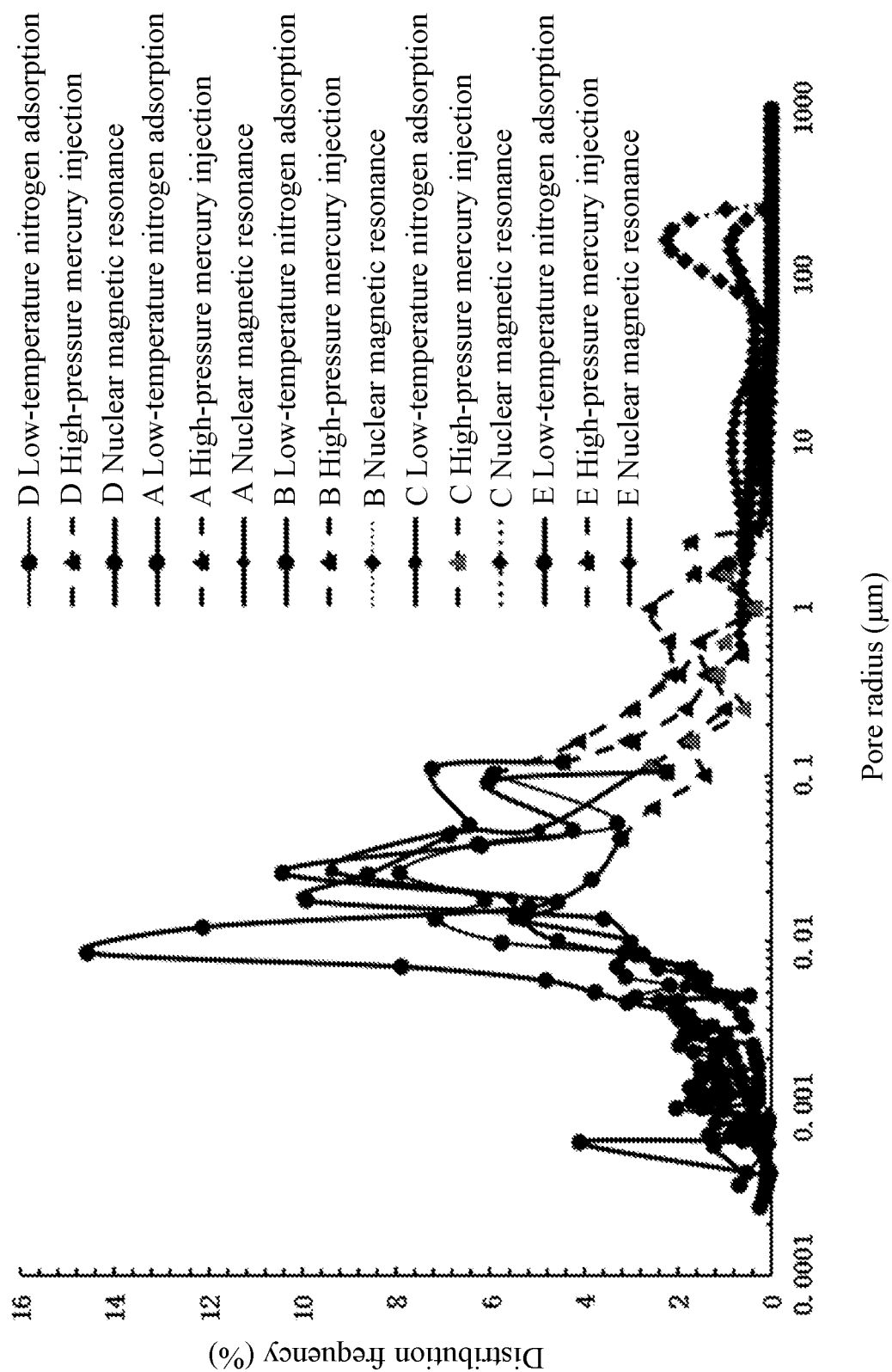
FIG. 3 illustrates a schematic normalized connection diagram of pore radii of different lithofacies according to an embodiment of the disclosure.

As shown in FIG. 3, FIG. 3 is a schematic normalized connection diagram of pore radii obtained by tests on different lithofacies using the method of the disclosure.

In an embodiment, the low-temperature nitrogen adsorption test is performed at a basic temperature of 77.35 kelvins (K), and a Barret-Joyner-Halenda (BJH) method is used to calculate the first pore radii. In the BJH method, the pore of the shale is considered as a columnar model, a distribution of pores being larger than 5 nm is calculated, and a diameter obtained from a Kelvin equation plus a liquid film thickness is a diameter of a pore throat. The high-pressure mercury injection test uses the standard non-wet-phase fluid mercury to simulate the crude oil. The high-pressure mercury injection test uses a cylindrical pore model as a foundation, mercury at room temperature is pressed in pores of a material (i.e., the shale) under a given pressure, when the given pressure increases to the capillary pressure, the mercury will continue to invade the pores, and sizes (i.e., radii) of the corresponding pores are measured by a pressure value applied from an external environment. Based on a Washbirn equation, a pore radius of a sample is inversely proportional to a pressure, and thus a curve of the capillary pressure can be obtained by continuously changing a pressure of the injected mercury. The nuclear magnetic resonance test uses the standard plunger sample vacuumed for 24 hours and saturated with 12 MPa pressure for 72 hours.

The disclosure considers pore structure characteristics of actual shale, and the pore structure characteristics from micropores to microcracks are involved. The disclosure can solve a problem of describing a characteristic of shale occurrence space with a complex pore structure and a strong heterogeneity, and the disclosure lays a foundation for precise evaluation of shale oil mobility. The method of the disclosure is easy to implement, has higher accuracy, and the method is more suitable for determining a lower radius limit of a movable throat of an unconventional oil reservoir, especially shale.

What is claimed is:

1. A method for determining a lower radius limit of a movable throat of shale, comprising:
   S1, performing a nitrogen adsorption test on a target shale to obtain first pore radii of the target shale;
   S2, performing a mercury injection test on the target shale to obtain second pore radii of the target shale;
   S3, performing a nuclear magnetic resonance test on the target shale to obtain third pore radii of the target shale;
   S4, obtaining a relationship diagram of distribution frequencies and pore radii according to the first pore radii, the second pore radii and the third pore radii;
   S5, distinguishing, according to the pore radii, data of the relationship diagram of the distribution frequencies and the pore radii to determine target frequency data, performing normalization processing on the target frequency data to obtain normalized frequency data, and determining a relationship curve of the normalized frequency data and the pore radii; and S6, determining a lower radius limit of a movable throat of the target shale according to the relationship curve of the normalized frequency data and the pore radii;

wherein S6 comprises:

S6-1, saturating a core of the target shale with crude oil to obtain a saturated core;

S6-2, heating and extracting the saturated core by using petroleum ether as an oil washing solvent to obtain shale oil, and taking a percentage of a volume of the shale oil to a pore volume of the core as a movable oil saturation; and S6-3, summing distribution frequencies corresponding to pore radii from larger to smaller in sequence according to the relationship curve of the normalized frequency data and the pore radii to obtain a cumulative distribution frequency from larger to smaller pores; in a situation that the cumulative distribution frequency from larger to smaller pores is equal to the movable oil saturation, obtaining a corresponding throat radius as the lower radius limit of the movable throat of the target shale.

2. The method for determining the lower radius limit of the movable throat of shale as claimed in claim 1, wherein step S1 comprises:

obtaining each of the first pore radii r according to a formula expressed as follows:

$$\ln \frac{p}{p_0} = \frac{2\gamma \bar{V}}{rRT}\cos\theta;$$

wherein $\bar{V}$ represents a molar volume of liquid; p represents a balance pressure; $p_0$ represents a saturation balance pressure; γ represents a surface tension of liquid nitrogen; R represents a universal gas constant; T represents an absolute temperature; and θ represents an angle between an adsorbate and an adsorbent.

3. The method for determining the lower radius limit of the movable throat of shale as claimed in claim 1, wherein step S3 comprises:

performing the nuclear magnetic resonance test on a standard plunger sample of the target shale vacuumed for 24 hours and saturated with 12 megapascals (MPa) pressure for 72 hours to thereby obtain each of the third pore radii r″ according to a formula expressed as follows:

$$r''=T_2\rho_2F_s;$$

wherein $T_2$ represents a T2 relaxation time of nuclear magnetic resonance; $F_s$ represents a dimensionless shape factor, wherein $F_s=2$; and $\rho_2$ represents a surface relaxation rate.

4. The method for determining the lower radius limit of the movable throat of shale as claimed in claim 2, wherein step S5 comprises:

S5-1, for the pore radii being in a range of 0-100 nanometers (nm), taking an intersection of a nitrogen adsorption curve and a mercury injection curve as a first demarcation point of the nitrogen adsorption curve and the mercury injection curve, determining the nitrogen adsorption curve as a curve before the first demarcation point, and determining the mercury injection curve as a curve after the first demarcation point;

for the pore radii being in a range of 100-2000 nm, taking an intersection of the mercury injection curve and a nuclear magnetic resonance curve as a second demarcation point of the mercury injection curve and the nuclear magnetic resonance curve, determining the mercury injection curve as a curve before the second demarcation point, and determining the nuclear magnetic resonance curve as a curve after the second demarcation point; and thereby obtaining three-segment pore radius-distribution frequency data;

S5-2, summing the three-segment pore radius-distribution frequency data to obtain a sum, taking the sum as a denominator, taking a distribution frequency of each of the pore radii as a numerator, and dividing the denominator by the numerator and multiplying by 100 percent (%) to obtain the normalized frequency data; and S5-3, obtaining the relationship curve of the normalized frequency data and the pore radii according to the normalized frequency data.

5. The method for determining the lower radius limit of the movable throat of shale as claimed in claim 1, wherein step S2 comprises:

simulating, by using a standard non-wet-phase fluid mercury, crude oil to perform the mercury injection test to thereby obtain each of the second pore radii r′ according to a formula expressed as follows:

$$r'=2\sigma \cos\theta'/Pc;$$

wherein Pc represents a capillary pressure; θ′ represents a wetting angle between mercury and the target shale; and α represents an interface tension between the mercury and air.

\* \* \* \* \*